US006291245B1

(12) United States Patent
Kopetzki et al.

(10) Patent No.: US 6,291,245 B1
(45) Date of Patent: Sep. 18, 2001

(54) HOST-VECTOR SYSTEM

(75) Inventors: Erhard Kopetzki, Penzberg; Christian Schantz, Thalhausen, both of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/344,888

(22) Filed: Jun. 25, 1999

(30) Foreign Application Priority Data

Jul. 15, 1998 (EP) .................................. 98113156
Oct. 9, 1998 (EP) .................................. 98119078

(51) Int. Cl.[7] ............................. C12N 15/74; C12N 1/20; C12N 15/64; C12Q 1/68; C12P 21/06; C12P 19/34; C07H 12/02; C07H 21/04
(52) U.S. Cl. ............................. 435/471; 435/6; 435/69.1; 435/91.1; 435/91.42; 435/252.33; 435/320.1; 536/23.1; 536/24.1
(58) Field of Search .................. 435/6, 69.1, 91.1, 435/91.32, 91.5, 91.51, 91.4, 91.41, 91.42, 170, 455; 536/23.1, 24.1; 935/31, 39, 43, 55

(56) References Cited

U.S. PATENT DOCUMENTS

| 4,689,406 | * | 8/1987 | Banks et al. ............................. 536/27 |
| 5,198,343 | | 3/1993 | DeGryse . |
| 5,843,772 | * | 12/1998 | Devine et al. ..................... 435/320.1 |

FOREIGN PATENT DOCUMENTS

| 2511032 | 2/1983 | (EP) . |
| 0 157441 | 10/1985 | (EP) . |
| 178 764 | 4/1986 | (EP) . |
| 0 185 512 | 6/1986 | (EP) . |
| 0 258 118 | 3/1988 | (EP) . |
| WO 8903427 | 4/1989 | (WO) . |
| WO 91/11523 | 8/1991 | (WO) . |
| WO 91/13971 | 9/1991 | (WO) . |
| WO 94/02607 | 2/1994 | (WO) . |

OTHER PUBLICATIONS

Gentz et al. 1981. Proc. Nat'l Acad. Sci. USA vol. 78, No. 8 pp. 4936–4940.*
Amann et al 1983. Gene vol. 25, pp. 167–178.*
Promega Protocols & Applications Guide. 2nd Ed. 1991. pp. 312–367. Ed. by D. Titus. Publi.—Promega.*
Sambrook, et al. Molecular & Cloning: A Lab Manual. 1989. 2nd Edition. pp. 17–17–17–24 Publisher—Cold Spring Harbor Lab. Press.*
De Boer et al 1983 Proc Nat'l Acad Sci. USA vol. 80, pp. 21–25.*
Backman, K. et al., Cold Spring Harbor Symposia Quant. Biol. 43(1978) pp. 69–76.
Beck, E. et al., Gene 16 (1981) pp. 35–58.
Grodberg, J. et al., J. Bacteriol. 170(1988) pp. 1245–1253.
Hamilton, C.M. et al., J. Bacteriol. 171 (1989) pp. 4617–4622.
Kopetzki, E. et al., Mol. Gen. Genet. 216 (1989) pp. 149–155.
Kopetzki, E. et al., Yeast 5 (1989) pp. 11–24.
Rose, M. et al., Gene 29 (1984) pp. 113–124.
Schwarz, E. et al., Nature 272 (1978) pp. 410–414.
Struhl, K. et al., Proc. Natl. Acad. Sci. USA 73 (1976) pp. 1471–1475.
Stuber, D. et al., Immunological Methods IV (1990) pp. 121–152.
Sutcliffe, G. et al., Quant Biol. 43 (1979) pp. 77–90.
Tschumper, G., Gene 10 (1980) pp. 157–166.
Turnbough, C. L. Jr. et al., J. Biol. Chem. 262 (1978) pp. 10239–10245.
Yanofsky, C. et al., Nucl. Acids Res. (1981) pp. 6647–6668.
Journal of Biotechnology 18 (1991) pp. 29–40.
Yeast, vol. 2 pp. 163–167 (1986).
Gene, 8 (1979), pp. 17–24.
Gene, 74 (1988) pp. 527–534.
Abstract corresponding to FR 2511032.

* cited by examiner

*Primary Examiner*—Robert A. Schwartzman
*Assistant Examiner*—Jane Zara
(74) *Attorney, Agent, or Firm*—George W. Johnston; William H. Epstein (57) ABSTRACT

A prokaryotic expression vector including an origin of replication, at least one eukaryotic auxotrophy marker gene which encodes an enzyme required for the synthesis of a product necessary for the survival of at auxotrophic prokaryote under the control of a eukaryotic promoter, a foreign gene under the control of a prokaryotic promoter, and one or more transcription terminators.

16 Claims, 3 Drawing Sheets

```
XhoI
ctcgagAAATCATAAAAAATTTATTTGCTTTGTGAGCGGATAACAATTATAATAGATTCA        60
|---    T5-P_{N25/03/04}    --->

EcoRI              NdeI SalI
ATTGTGAGCGGATAACAATTTCACACAGAATTCATTAAAGAGGAGAAATTAcaTATGgtc       120
                                              RBSII XmaI   EcRV  CelII
gacccggggatatcGCTGAGCTTGGACTCCTGTTGATAGATCCAGTAATGACCTCAGAA        180
                       |---    λ-T0 Terminator   --->

CTCCATCTGGATTTGTTCAGAACGCTCGGTTGCCGCCGGGCGTTTTTTATTGGTGAGAAT       240

BamHI
Cggatcc                                                            247
|
```

HOST-VECTOR SYSTEM

BACKGROUND OF THE INVENTION

Known and typical prokaryotic expression plasmids contain, in addition to one or several antibiotic resistance gene(s), additional DNA sequences which are not required and burden the cell metabolism. These include DNA sequences resulting from the cloning process, DNA segments that are relics from multipurpose vectors such as specific promoters for the in vitro synthesis of mRNA and specific phage replication origins for the synthesis of single stranded DNA and extend to rudimentary duplicated vector sequences which can be the cause of undesired plasmid rearrangements.

The presence of a plasmid and in particular of an expression vector is an additional metabolic burden for the cell. This results in a selection pressure which favours the formation of cells without plasmids. One method of selecting for cells containing plasmids is antibiotic selection.

Antibiotics such as ampicillin, tetracycline, kanamycin and chloramphenicol are usually used for selection. The use of β-lactam antibiotics such as ampicillin is especially problematic in the production (fermentation) of therapeutic products.

For the reasons discussed above antibiotic plasmid selection, especially by means of β-lactam antibiotics, is not favored in recent methods. In some cases a host/vector system has been developed that proved to be so stable that it was possible to omit a plasmid selection during the preculture and during the main fermentation (Weir, A. N. C. and Mountain, A., EP 0651803). However, as a rule this is associated with a reduced product yield. In cases in which antibiotic selection is indispensable, tetracycline is often used as an alternative to ampicillin (Carter, P. et al., 1992). In contrast to the β-lactam antibiotics, the tetracyclines are not reactive chemical compounds and cannot be inactivated by enzymatic modification during fermentation. The tetracycline resistance gene codes for a protein which modifies the bacterial membrane and thus prevents the antibiotic from entering the cell.

Selection systems have been developed that do not use antibiotic resistance, instead exploiting complementation technology. Struhl, K. and coworkers (Struhl, K. et al., 1976) using imidazole glycerol phosphate dehydratase (HIS3) as an example, show that an appropriate *E. coli* mutant (hisB) can be directly complemented by means of plasmids containing yeast DNA and that the yeast enzyme coded by HIS3 is functionally expressed in *E. coli*. This ability of genes to complement mutations in *E. coli* was used as a selection criterion to clone for example (complementation cloning) other yeast genes (LEU2, URA3, TRP5 and ARG4).

*E. coli* host strains with a stable mutation (reversion rate >$10^{-10}$; preferably non-revertable deletion mutants) are required for selection by complementation. However, the reversion rate of known mutations is of the order of magnitude of <$10^{-10}$ (Schlegel, H. G., 1981).

The known *E. coli* laboratory strains differ with regard to their genotype in individual mutations which in many cases were produced by undirected mutagenesis by radiation (X-ray or UV radiation), chemical mutagens (e.g. base analogues, nitrous acid and alkylating compounds) or biological techniques (e.g. phage Mu and transposon mutagenesis (Bachman, B. J., 1986).

SUMMARY OF THE INVENTION

We have developed a stable prokaryotic (preferably *E. coli*) host/vector system (expression system) which avoids plasmid selection by antibiotics. The selection principle is based on complementation of a stable auxotrophy of the prokaryotic host cell by an adequate yeast gene.

The invention concerns a minimal prokaryotic expression vector which cannot be homologously recombined with the genome of prokaryotic organisms. The vector contains:
a) an origin of replication,
b) an auxotrophy marker gene,
c) a promoter which is functionally active in prokaryotes and
d) a foreign gene (foreign sequence) to be expressed under the control of the said promoter.

Therefore the invention concerns new prokaryotic expression systems which enable antibiotic-free selection and their use for the production of recombinant proteins. The invention is directed to a prokaryotic expression vector which comprises:
a) An origin of replication;
b) at least one eukaryotic auxotrophy marker gene under the control of a eukaryotic promoter;
d) a foreign gene under the control of a prokaryotic promoter; and
e) one or more transcription terminators.

It is preferable that the prokarytic expression vector is not sufficiently large, in order to reduce the metabolic burden of the cell. The vector element used should preferably be of heterologous origin and very small to engage in homologous recombination with the genome of a prokaryotic host cell. In this regard, a desirable size for the vector of this invention is 2500 base pairs or less, to a lower limit set by the minimum size of an expression vector containing the elements listed above.

A preferred expression vector is assembled such that the auxotrophy marker gene and the foreign gene are oriented in opposite directions with the transcription terminator located between the auxotrophy marker gene and the foreign gene so positioned as to terminate transcription of both genes.

A preferred source of the auxotrophy marker gene of this invention is yeast, for example *Saccharomyces cerevisiae*. Particular marker genes useful in this invention are URA3 or TRP1. Accordingly, the preferred eukaryotic promoter is a yeast promoter. When the URA1 or TRP1 gene is being used, the promoters are part of the 5' flanking region of the URA3 or TRP1 gene.

Any prokaryotic promoter may be used for the expression of the foreign gene. A preferred prokaryotic promoter is T5-$P_{N25/03/04}$. In the context of this invention, prokaryotic promoter includes promoters derived from bacteriophages.

Any transcription terminator may be used. A preferred transcription terminator is derived from a bacteriophage, for example bacteriophage fd or λ-T0.

Any origin of replication may be used, however preferred are origin of replications from pBR or pUC plasmids.

This invention is also directed to prokaryotic auxotrophic host cells. The host cell of this invention contains a prokaryotic expression vector of this invention and has at least one mutation such that it is unable to express the product expressed by the auxotrophic marker gene in the expression vector. A preferred host cell is an *E. coli* cell, especially a host cell such as an *E. coli* cell which is unable to produce the product of the trpC gene or the pyrF gene. An especially preferred host cell contains a prokaryotic expression vector of this invention.

Such a prokaryotic host cell preferably produces sufficient amounts of the product of the genes URA3 or TRP1 to survive on minimal medium but does not produce an amount of such gene product which constitutes more than 1.0% of the total amount of protein produced by the cell. The URA3 or TRP1 protein produced can be assayed by SDS PAGE analysis cell lysates.

A BRIEF DESCRIPTION OF THE FIGURES

FIG. 1: Construction of E. coli trpC deletion mutants by a gene exchange technique. The sequences flanking the trpC gene to be deleted are integrated into the vector pMAK705. Only E. coli strains transformed by homologous recombination and integration of the plasmid into the chromosome and cultured at 44° C. with the addition of chloramphenicol survive since the plasmid cannot replicate (co-integrate formation) at 44° C. Subsequent culture at 30° C. under chloramphenicol selection leads to a second homologous recombination in which the plasmid is cut out of the chromosome. This break up of the co-integrate can lead to the initial plasmid pMAK705-trpD/B (A) or to a pMAK705-trpD/C/B plasmid derivative which additionally contains the trpC gene (B). The trpC gene on the E. coli chromosome is only deleted in case B.

DETAILED DESCRIPTION OF THE INVENTION

A prokaryotic expression vector as used in this invention is a vector such as a plasmid which when introduced into a host cell (e.g. a cell to which the vector is not native) is capable of causing expression of a target gene carried by the vector, whose expression is desired (the "foreign gene"). Any sequences are suitable as a foreign sequence within the sense of the invention. Such nucleic acid sequences preferably code for polypeptides which have an effect on metabolism in the human body. Such proteins or polypeptides are preferably therapeutically relevant polypeptides such as cytokines, proteins or protein hormones. Genes encoding such relevant polypeptides are generally available from suppliers, or sequences for such genes are available in databases or literature for synthesis. Otherwise, genes encoding proteins of interest may be isolated by known methods.

Any standard expression vector may be used, such as plasmids, cosmids or vectors derived from bacteriophages. However plasmids are preferred. Plasmids are extra chromosomal (episomal) circular double-stranded DNA molecules which have a length of several thousand nucleotide building blocks and occur in several to several hundred copies per cell. They have a DNA segment, the so-called origin of replication, which enables an autonomous plasmid replication/amplification independent of the chromosomal DNA replication. Various standard plasmids are available from suppliers and in the literature. It is well known technology to integrate selected genes into plasmids for expression.

The host cell used in this invention is an auxotrophic microorganism, e.g. one which due to mutation can no longer synthesize a substance (such as an amino acid) necessary for its nutrition and, as a result, requires an external supply of that substance—for example via the medium used for culturing. The mutation is usually found in a gene encoding one of the enzymes needed in the metabolic pathway for the substance. Any standard prokaryotic host cell can be used, however a preferred host cell is E. coli.

The auxotrophy marker gene which is part of the vector is understood as a gene which enables cell growth of such auxotrophic host cells under selective culture conditions by encoding an enzyme required for the synthesis of a product necessary for the survival of an auxotrophic prokaryote on a selective medium used for cell culturing. Particularly preferred marker genes are heterologous eukaryotic genes, preferably yeast genes, which compensate a defect (mutation) in an essential metabolic path of the host cell. Any pairing of a eukaryotic marker gene which is capable of complementing the corresponding gene which is nonfunctional in an auxotrophic host prokaryote may be useful in this invention. Genes encoding enzymes for amino acid biosynthesis are preferred, for example the yeast HIS2 or LEU2 or ARG4 genes to complement a mutant prokaryote which is unable to produce histidine or leucine or arginine. Such genes are known in the art and are available from suppliers, or their sequences can be obtained from databases or literature.

With E. coli as the host organism, mutants with a defect in the tryptophan, leucine or uracil biosynthetic pathway are preferred which can then be complemented by the marker gene. There are a large number of techniques available for producing E. coli mutants which are suitable for the construction of E. coli host strains. They range from mutagenesis of the whole cell followed by selection of the desired phenotype to the specific mutagenesis of individual bases or of exactly defined gene or genome sections (see last paragraph of Background). The methods are described by Miller, J. H. (1972), Neidhardt, F. C. et al. (1987) and Winnacker, E.-L. (1985).

In this connection the transcription of the auxotrophy marker gene and the transcription of the foreign gene to be expressed are preferably in opposite directions. It is also preferred that the marker gene is heterologous to the prokaryotic organism used as the host cell. It is additionally preferred that the expression of the auxotrophy marker gene in the host/vector system described in the invention is 1% or less of the total protein expressed in the host cell when the auxotrophy is complemented in the host cell. The expression of the auxotrophy marker gene can be analysed by SDS PAGE, staining with Coomassie dye and visual inspection of the protein pattern of the cell lysate.

Minimizing expression of the auxotrophy marker gene reduces the metabolic burden on the host cell, providing comparatively better yield of the foreign gene. Determination of the percent total protein may be accomplished by analysis of all the protein produced by the host cell by well known methods, determining the amount of marker gene product, and thereby determining the percent total protein. Preferred host cells of this invention express 1.0% or less of the marker gene. Using a eukaryotic promoter for the marker gene also helps minimize its expression relative to the foreign gene which has a prokaryotic promoter.

In a preferred embodiment the expression vector according to the invention is characterized in that the reading frame of the auxotrophy marker gene and of the gene to be expressed have opposite orientations and are terminated by the same transcription terminator or several transcription terminators arranged in series.

By opposite orientation is meant that one gene is inserted in the 5' to 3' orientation and is read clockwise the other gene is inserted in the 3' to 5' orientation and is read counterclockwise. The transcription terminators are placed between the genes such that the 3' end of each gene is followed by a transcription terminator. It is well known to insert genes into vectors, for example by using predetermined restriction sites. The orientation of the gene to be inserted can be predetermined by placing a different restriction sites on each end of the gene (corresponding to restriction sites in the plasmid). When the gene expression cassette and plasmid are exposed to the appropriate restriction enzymes, the gene orients itself as desired. The purpose of opposite orientation is to guarantee efficient transcription, termination, e.g. by two terminators in tandem, and to prevent read through of the strong bacterial promoter.

A further subject matter of the invention is a prokaryotic auxotrophic host cell which contains a vector according to the invention wherein this host cell has a mutation (deletion) in a gene which is complemented by the selection marker gene of the expression vector and the deletion or mutation has the effect that no functional product of the said host cell gene is expressed. The deletion is preferably located in an essential chromosomal gene which corresponds to the auxotrophy marker gene of the expression vector. A further subject matter of the invention is a method for producing a prokaryotic expression system which comprises introducing an expression vector according to the invention into a prokaryotic auxotrophic cell with a deletion in a gene which corresponds to the auxotrophy marker of the expression vector where the deletion or mutation has the effect that no functional product of the said host cell gene is expressed.

A further subject matter of the invention is a process for the production of a heterologous protein by heterologous expression of a desired protein by using an expression vector according to the invention in a host cell according to the invention and isolation of the expression product from the cells or the supernatant wherein the fermentation is carried out in a minimal medium or in a synthetic complete medium.

A farther subject matter of the invention is a process for the production of a prokaryotic expression system which is characterized in that an expression vector according to the invention is introduced into a prokaryotic host cell with a mutation in a chromosomal gene which is complemented by the auxotrophy marker gene of the expression vector and the chromosomal mutation has the effect that no functional product of the said chromosomal host cell gene can be expressed.

In the present invention a new E. coli host/vector system based on the complementation of an essential chromosomal E. coli auxotrophy (trpC, pyrF) by the plasmid-coded expression of a suitable yeast gene (TRP1, URA3) was developed instead of the usual selection with antibiotics. In addition:
i) new expression vectors optimized (minimized) with respect to size were constructed using minimal functional elements (selection marker, origin of replication and expression cassette),
ii) non-revertable host strains were isolated by homologous recombination (deletion) of a desired chromosomal E. coli gene (trpC, pyrF) and
iii) the components of the new host/vector system (expression plasmids and host strains) were checked with regard to function and performance on the basis of the expression of a model gene (interferon-α-2b).

For this:
i) E. coli host strains with stable mutations(deletions) of the chromosomal genes trpC and pyrF and
ii) vectors which contain the complementing yeast genes TRP1 (Tschumper, G., 1980) or URA3 (Rose, M., 1984) were constructed.

Double mutants or deletion mutants are preferably constructed as stable host strains.

The minimal vectors according to the invention, consisting of promoter, polylinker, terminator, auxotrophic marker and origin of replication (without foreign gene to be expressed), are preferably very small (about 2500 bp, and preferably smaller than 2000 bp) and only contain the absolutely essential elements of an expression plasmid i.e. an origin of replication, a heterologous selection marker gene and a heterologous expression cassette and these have the smallest possible size to avoid homologous recombination with the genome of the prokaryotic host cell. A homologous recombination within the meaning of the invention is understood as the exchange of DNA sequences between the vector according to the invention and the genome of the host cell. Homologous recombination can occur when there is a considerable sequence compatibility (at least 50–1000 bp) between the vector and genome. Less agreement in the sequence (below 50 bp) does not lead to homologous recombination to a detectable extent within the meaning of the invention. Homologous recombination must be avoided to prevent plasmid rearrangement.

Homologous recombination occurs via homologous sequences. Therefore homologous sequences (identical sequences) on the plasmid and genome should be avoided or must be as short as possible. The homologous sequences on the vectors according to the invention and the E. coli genome are too small to engage in any significant recombination with the host genome. This is ensured by minimizing the size of the homologous sequences, which in turn reduces the chance of a recombination event by minimizing the probability that sufficient sequence compatibility will exist. That recombination has not occurred can be determined by known methods, for example by plasmid restriction analysis or by sequencing.

Examples of suitable host cells are E. coli TrpC mutants which are characterized by an inactive N-(5'-phosphoribosyl)-anthranilate isomerase (EC 5.3.1.24) and pyrF mutants which are characterized by an inactive orotidine-5'-phosphate decarboxylase (EC 4.1.1.23). The mutants are incapable of synthesizing tryptophan or uracil and can therefore not grow on nutrient media which lack these components. In contrast they exhibit normal growth on complete medium since tryptophan and uracil are present in adequate amounts.

The auxotrophic trpC and pyrF mutants are complemented by a plasmid according to the invention which contains the absent or defective gene for the respective biosynthesis without a mutation. However, the complementing genes are not derived from E. coli but from the yeast Saccharomyces cerevisiae. These eukaryotic marker genes include their native yeast promoters. They code for the same enzymes as the corresponding E. coli genes. Due to the poor function of the yeast promoters, their transcription in E. coli is less than the transcription of the host's endogenous analogous E. coli genes. The plasmid-coded expression of the URA3 yeast gene ($pBR_{322}$ plasmid derivative) is for example only one third of the expression of the analogous chromosomal pyrF gene (Rose, M., 1984). This has the advantage that the marker genes are not overexpressed despite the gene dose effect and the cell is not additionally metabolically stressed.

A particular stable *E. coli* host/vector system of this invention avoids plasmid selection by antibiotics. The selection principle is based on the complementation of a stable *E. coli* auxotroph by an adequate yeast gene as described above.

The *E. coli* host strains preferably contain a stable, preferably non-revertable mutation (deletion) in the chromosomal genes trpC and/or pyrF and an expression plasmid which contains the complementing yeast genes TRP1 and/or URA3.

The basic expression plasmids are characterized by:
i) the absence of antibiotic resistance genes and
ii) their very small size (<2000 bp).

They only contain the absolutely essential elements for replication in *E. coli* and expression of a desired gene:
i) an origin of replication,
ii) a selection marker gene and
iii) a prokaryotic or eukaryotic expression cassette (gene therapy), and the size of these plasmid elements is as minimal as possible.

The Origin of Replication

The origin of replication for the autonomous replication of the plasmid in the cell is derived from any known prokaryotic plasmid, preferably from a natural *E. coli* plasmid. Most of the *E. coli* plasmids used today are derivatives of the cloning vector pBR$_{322}$ (Boliver, F. et al., 1979) the replicon of which (origin of DNA replication) is based on the plasmid pMB1 (Sutcliffe, G. et al. 1979) which only differs slightly from the plasmid ColE1. The replication of the plasmid pBR$_{322}$ is also referred to as replication of the ColE1 type (Backman, K. et al., 1978). The minimal DNA sequence which is responsible for an autonomous replication of the pBR$_{322}$ plasmid was reduced by Backman, K. et al. 1978 to a 580–650 bp long DNA sequence. The plasmid copy number per cell is determined by the type of replication origin. Depending on the number of copies per cell that can be achieved, one refers to low copy number (ca. 10 copies, pACYC plasmids), medium copy number (ca. 50 copies, pBR plasmids) and high copy number (ca. 500 copies, pUC plasmids) plasmids. The high copy number origin of replication of the pUC plasmids is only based on a point mutation of the pBR origin of replication (Chambers, S. P. et al., 1988). The expression yield of a gene generally correlates with the copy number of the gene to be expressed. Such origins of replication are well known and their sequences are readily available. Depending on the desired number of plasmids per cell, a higher or lower copy number plasmid can be selected.

The Expression Cassette

An expression cassette for expression of a desired foreign gene (heterologous transcription unit) is composed of:
i) a promoter,
ii) a ribosomal binding site,
iii) a multiple cloning cleavage site and
iv) a transcription terminator (rho-independent termination).

The multiple cloning cleavage site serves to insert the foreign gene (structural gene) to be expressed and for this purpose it is composed of at least two restriction endonuclease cleavage sites that are present only once in the vector. The cleavage sites that face the promoter preferably contain the nucleotide sequence for an ATG start codon in their recognition sequences, such as the recognition sequences for the restriction enzymes NcoI, BspHI, SpHI and NdeI. This facilitates the precise connection between promoter and structural gene.

A promoter is a DNA fragment which contains the control signals for the start of mRNA synthesis and the frequency with which this mRNA molecule is to be formed and is functionally active in an expression cassette. A typical natural *E. coli* promoter is 80–300 base pairs long and contains several characteristic (homologous) regions which are common to the various promoters and which have been determined by sequence comparisons (Rosenberg, M. and Court, D., 1979; Harley, C. B. and Reynolds, R. P., 1987). The highly conserved regions are:
i) the recognition site for the RNA polymerase with the motif 5'-TTGACA-3', which is 35 base pairs before the start of the mRNA synthesis,
ii) the Pribnow Schaller box or so-called TATA box with the codonical prototype sequence 5'-TATAAT-3' which is located 10 base pairs before the start of the mRNA synthesis and
iii) an AT-rich region around position "–43" in strong promoters.

Depending on the frequency with which a promoter is read one refers to weak and strong promoters. A distinction is also made between constitutive and regulatable (inducible, derepressible) promoters. A good promoter in terms of the industrial production of proteins is usually a strong, strictly regulated promoter that is inactive during cell multiplication and which can be specifically switched on as required e.g. at the end of a fermentation. These requirements of a very high and at the same time strictly controllable promoter activity have led to the construction of the hybrid promoters that are nowadays preferably used. In the case of the tac hybrid promoter which can be readily regulated, the "–35" region of the strong constitutive trp promoter was fused with a "–10" region of the inducible lac promoter (DeBoer, H. A. et al., 1983; Amann, E. et al., 1983). A further example is the T5-P$_{N25/03/04}$ hybrid promoter (Stüber, D. et al., 1990) which is based on a strong constitutive T5 bacteriophage promoter and was reconstructed by combination/insertion of two lac operators (lacO) to form a strong promoter that can be readily regulated. The tac as well as the T5-P$_{N25/03/04}$ hybrid promoter are negatively regulated by the lacI repressor which prevents transcription of the promoter by interaction with the lac operator(s). Addition of the natural inducer lactose or of the very potent non-metabolizable lactose analogue isopropyl-β-D-thiogalactopyranoside (IPTG) leads to detachment of the lacd repressor and thus to formation of the desired mRNA and protein synthesis.

Promoters such as those described above are obtained from prokaryotic/bacteriophage sources. Such promoters are used in vectors of this invention for expression of the foreign gene whose product is desired. Eukaryotic promoters are also available. These promoters are used for expression of the auxotrophic marker genes. This ensures that the foreign gene is better expressed than the marker gene, since prokaryotic promoters perform better in a prokaryotic host than do eukaryotic promoters. A useful source of eukaryotic promoters is the 5' flanking region of the eukaryotic marker gene, as shown in the Examples that follow. In general promoters are well known and promoter sequences are available from databases, literature, or suppliers.

Transcription terminators are well known DNA sequences of 50–100 base pairs in length which give the RNA polymerase the signal for termination of the mRNA synthesis. They are structurally characterized by formation of a hairpin-shaped secondary structure resulting from complementary base pairing (mostly G/C-rich). Functionally they act independently of the orientation. Very efficient (strong)

terminators at the 3' end of an expression cassette are advisable to prevent the RNA polymerase from reading through particularly when using strong promoters. Inefficient transcription terminators can lead to the formation of an operon-like mRNA which can cause undesired expression of plasmid-coded genes. Furthermore the secondary structure at the 3' end of the mRNA caused by the terminator impedes degradation by 3' exonucleases (Higgins, C. F. et al., 1993) which can increase the half-life of the mRNA and consequently also increase the amount of synthesized protein. Examples of often used transcription terminators are the terminator T0 of the bacteriophage λ (Schwarz, E. et al., 1978), the fd bacteriophage terminator (Beck E. and Zink, B., 1981) and the terminator T1 of the *E. coli* rrnB operon. (Brosius, J. et al., 1981).

A ribosomal binding site (RBS) is also required for efficient initiation of protein biosynthesis. It comprises the well known sequence from the ATG start codon up to the so-called Shine Dalgarno sequence with the consensus motif AGGA. The distance between the ATG start codon and the SD sequence varies between 5–15 base pairs and is A/T-rich. The distance between the starting point of mRNA synthesis and the ATG translation start codon varies as a rule between 15–80 base pairs.

A stable non-revertible auxotrophy marker was introduced into host strains by the directed deletion of the complete gene or of a large gene fragment by means of homologous recombination according to the method of Hamilton C. M. et al., 1989. The original genotype is preserved in this technique i.e. no additional mutations are introduced into the *E. coli* genome. The principle of the gene exchange technique is elucidated in more detail using the construction of a tryC deletion mutant as an example.

It is intended for example to delete the complete trpC gene (1355 bp) from the tryptophan operon of *E. coli* (Yanofsky, C. et al., 1981). For this the flanking regions (700–800 bp in each case) of the trpC gene are amplified by means of PCR using appropriate primers and chromosomal *E. coli* DNA as the template. The overhangs of the primers contain singular cleavage sites for restriction enzymes in order to ligate the amplified DNA fragments of the genes trpD and trpB into the vector pMAK705 in a direct fusion. The vector pMAK705 is characterized by a temperature-sensitive origin of replication (origin of replication from pSC101) which is inactive at 44° C. and by a chloramphenicol resistance gene. In order to delete the chromosomal trpC gene, the pMAK705-trpD/B plasmid is transformed into the desired *E. coli* strain. A prerequisite for a homologous recombination between the plasmid and *E. coli* chromosome is a recombination-competent *E. coli* strain (recA+ genotype). Strains with a recA− genotype cannot carry out a homologous recombination and are therefore unsuitable. The transformed cells are cultured at 44° C. in the presence of chloramphenicol. Since the plasmid does not replicate at 44° C. due to its temperature-sensitive origin of replication (ori$^{ts}$), only those cells survive which have integrated the vector into the chromosome for example by means of homologous recombination.

Figure 1:
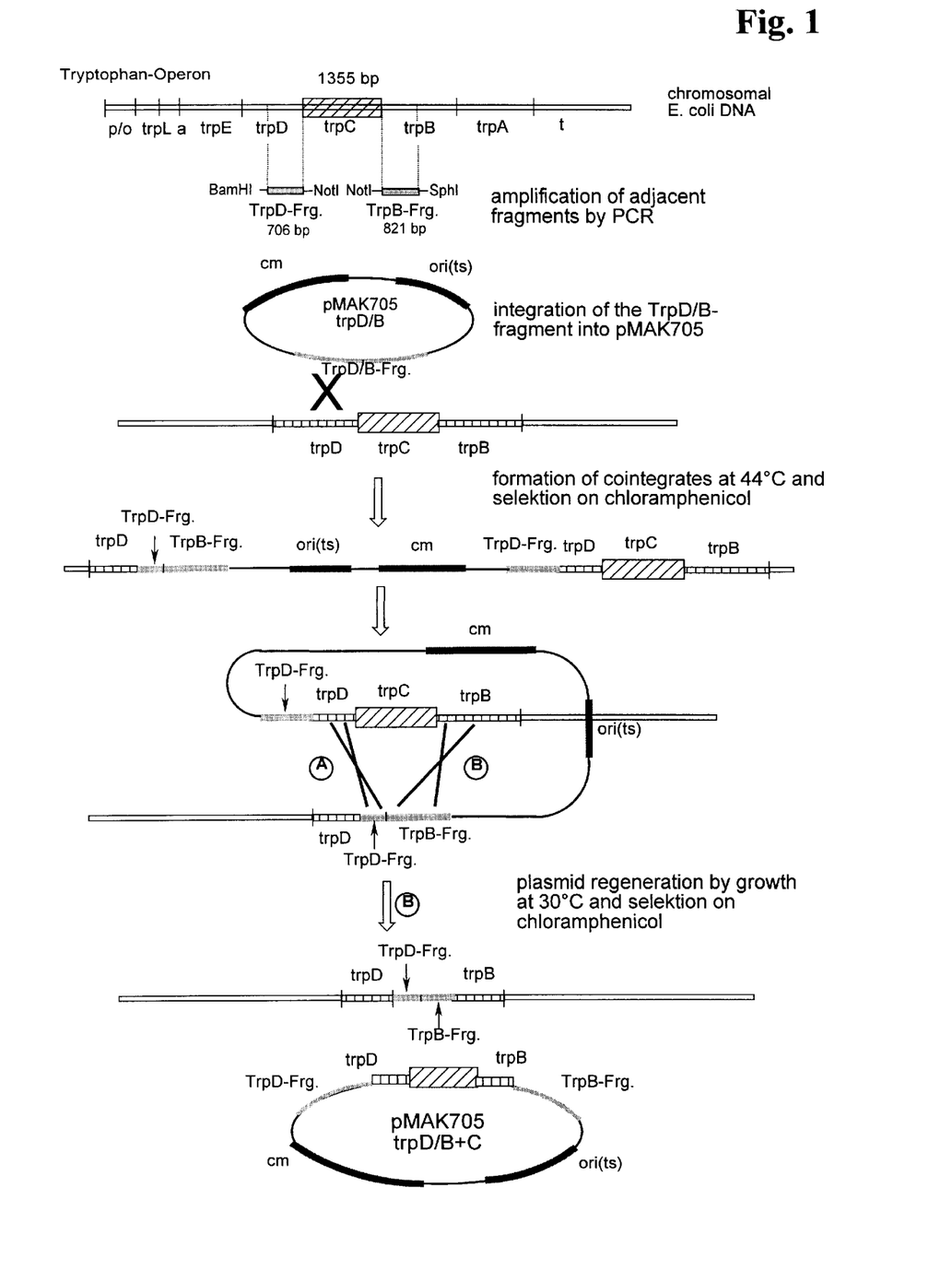
Figure 2:
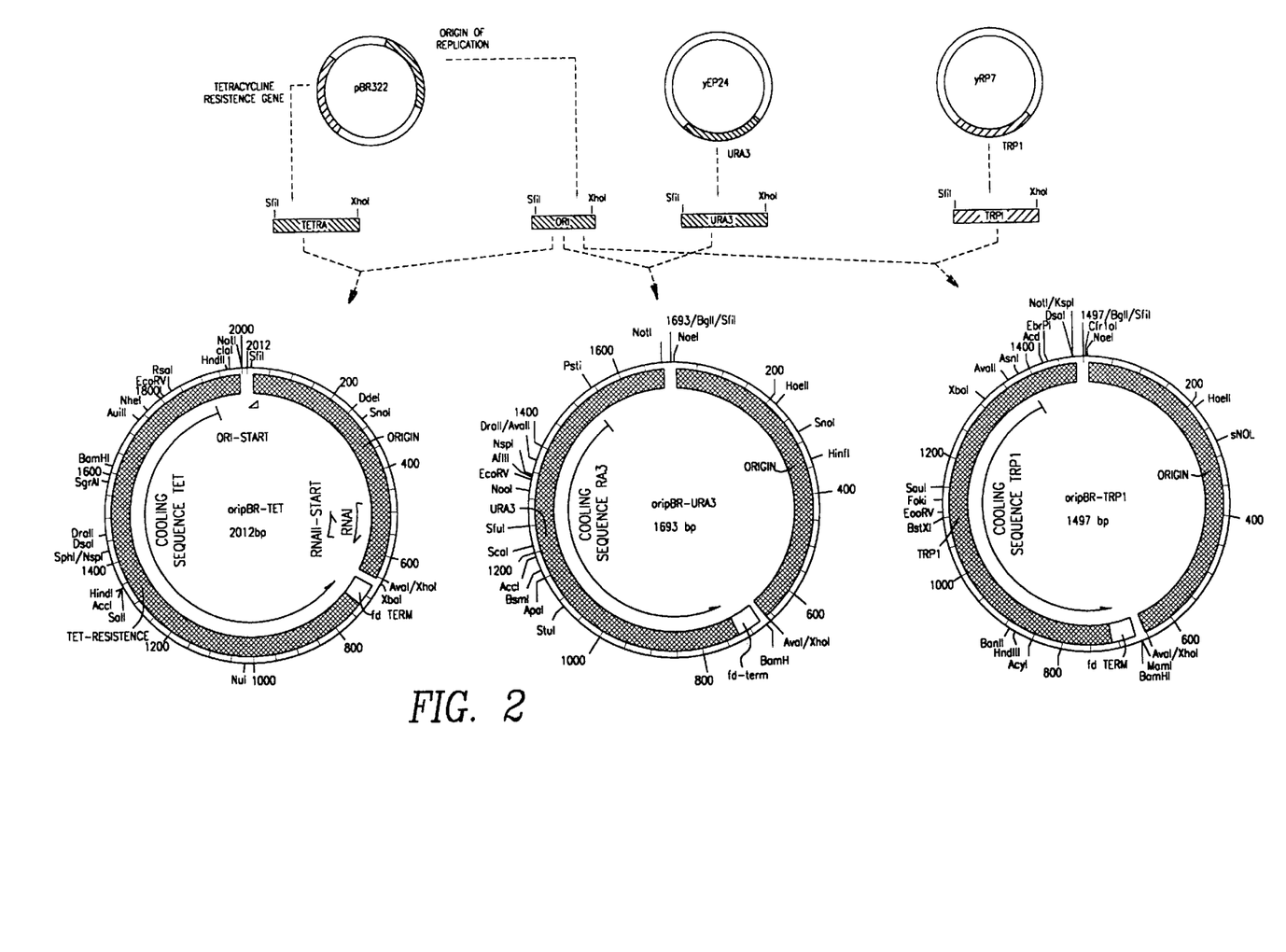
FIG. 2: Construction of the base vectors OripBR-TRP1, OripBR-URA3 and OripBR-TET: the plasmids OripBR-TRP1 (1497 bp), OripBR-URA3 (1697 bp) and OripBR-TET (2012 bp) are formed utilizing the cleavage sites SfiI and XhoI by ligating the marker genes TET, URA3 and TRP1 isolated from the plasmids $pBR_{322}$, yEP24 and yRP7 with a DNA segment containing the origin of replication from $pBR_{322}$.

The co-integrates are isolated and cultured under chloramphenicol selection over several passages at 30° C. The chromosomally localized origin of replication of the plasmid pMAK705-trpD/B which is active at this temperature leads to a drastic reduction in the growth rate of the co-integrates. Cells which have removed the plasmid from the chromosome by a second recombination event grow normally again. They contain the plasmid detached from the chromosome which replicates at 30° C. in the presence of chloramphenicol. The result is that cells containing plasmids overgrow the co-integrates and dominate in the culture after several passages. As elucidated in FIG. 1, the integrated plasmid can be detached from the chromosome in two different ways A and B. The plasmid then contains the gene trpC (B) to be deleted or it is again present in its original form in the cell (A) depending on the homologous recombination event. Cells which contain a plasmid with the chromosomal trpC gene very probably have the desired trpC deletion. They are identified by restriction analysis of the plasmids and are cured of the plasmid by a single culture at 44° C. and several cultures at 30° C. in the absence of chloramphenicol. Subsequently the clones are tested with regard to trpC auxotrophy by plating out the individual colonies on a medium with and without tryptophan (replica plating).

Special *E. coli* Host/Vector Systems and Host Strains

An extremely strictly regulated host/vector system was developed especially for the expression of proteins that are toxic for *E. coli* in order to prevent a basal expression of a gene which may still cause interference. The T7 polymerase system of Studier, F. et al., 1990 is based on a special RNA polymerase from the bacteriophage T7 which is absolutely selective and specific for the T7 promoter. Since the host's *E. coli* RNA polymerase does not recognize this T7 promoter, the T7 polymerase is provided at the time of induction by i) infecting the culture with a suitable phage such as e.g. the λ bacteriophage derivative CE6 or ii) by inducing a chromosomally-integrated T7 polymerase under lacUV5/lacI promoter control.

The special *E. coli* host strains BL21(DE3) and HMS174 (DE3) containing a T7 polymerase gene were constructed by chromosomal insertion of the lysogenic λ bacteriophage derivative DE3. This system which is often used in research laboratories is less suitable for industrial purposes because:

i) only a limited number of host strains (2) are available, ii) the DE3 lysogen is not absolutely stable in a fermenter and iii) the growth of the cells stagnates after the induction and consequently a growth to high cell densities is difficult.

The following examples, publications, sequence protocols and figures further elucidate the invention the protective scope of which results from the patent claims. The described methods are to be understood as examples which still describe the subject matter of the invention even after modifications.

General Methods

Standard methods were used to manipulate DNA as described in Sambrook, J. et al. (1989) In: Molecular Cloning: A Laboratory Manual. Cold Spring Harbor Laboratory Press, Cold, Spring Harbor, N.Y. The molecular biological reagents were used according to the manufacturer's instructions.

The origin of replication from the vector pBR$_{322}$ (medium copy number) and from the vector pUC20 (high copy number) were used as the origin of replication. The minimal DNA sequence for the autonomous replication of these plasmids is between 580–650 bp (Backman, K. et al., 1978).

The yeast genes TRP1 and URA3 were selected as selection marker genes. The tetracycline resistance gene was used to construct isogenic standard reference plasmids.

EXAMPLE 1

Construction of the Base Vectors OripBR-TRP1, OripBR-URA3 and OripBR-TET 1.1 Construction of the Base Vector OripBR-TRP1

The plasmid OripBR-TRP1 was composed of two DNA fragments which were obtained by the polymerase chain reaction (PCR) according to the method of Mullis, K. B. and Faloona, F. A., 1987. In a first PCR reaction the origin of replication of the plasmid $pBR_{322}$ from bp position 2517–3160 according to the publication of Sutcliffe J. G., 1979 was amplified using the primers N1 (SEQ ID NO:1) and N2 (SEQ ID NO.2).

SfiI
        N1: 5'-AAAAAAGGCCATATA GGCCGGCCGCGTTGCTGGCGTTTTC-3'
    XhoI
        N2: 5'-AAAAAA CTCGAGGAGCGTCAGACCCCGTAGAAAAG-3' and $pBR_{322}$ as the template DNA. A singular SfiI restriction endonuclease cleavage site was introduced by means of the 5' overhanging end of the PCR primer N1 and a singular XhoI restriction endonuclease cleavage site was introduced by means of the 5' overhanging end of the PCR primer N2.

The TRP1 yeast gene (5' flanking region and the TRP1 structural gene) from bp position 22–777 according to the publication of Tschumper, G. and Carbon, J., 1980 was amplified in a second PCR reaction using the primers N3 (SEQ ID NO:3) and N4 (SEQ ID NO:4)

SfiI NotI
        N3: 5'-AAAAAAGGCCATATA GCGGCCGCGGAGAGGGCCAAGAGGGAGGG-C-3'
    XhoI BamHl fd-terminator
        N4: 5'-AAAAAACTCGAGATATGGATCC TCTCCAAAAAAAAAGGCTCCAAAAGGAGC-CTTTAATTGTATCGGTTTATTTA CTATTTCTTAGCATTTTTGACGAAATTTGC-3'
    EndEnd and YRP7 (Kopetzki, E. et al., 1989) as the template DNA. A singular SfiI cleavage site and NotI cleavage site were introduced by means of the 5' overhanging end of the PCR primer N3 and a second translation stop codon, the fd transcription terminator of the bacteriophage fd from position 1522–1570 (Beck, E. and Zink, B., 1981) and two singular restriction endonuclease cleavage sites (MAKHI and XhoI) were introduced at the 3' end of the coding region of the TRP1 structural gene by means of the 5' overhanging end of the PCR primer N4.

The two PCR fragments digested with SfiI and XhoI were ligated after purification by agarose gel electrophoresis. Afterwards the *E. coli* K12 strain JA300 (thr, leuB6, thi, thyA, trpC117, hsrK, HsmK, strR; DSMZ 4776) (source: "Deutsche Sammlung für Mikroorganismen und Zellkulturen GmbH) was transformed by means of calcium chloride according to the method of Hanahan, D., 1983 or by electroporation according to the protocol of Fiedler, S. and Wirth, R., 1988. The transformants were selected on agar plates in M9 minimal medium (preparation: see Sambrook, J. et al., 1989) and 0.5% (w/v) casamino acids (acid-hydrolysed casein contains no tryptophan) from the Difco Company and subsequently grown in liquid culture. The desired plasmid OripBR-TRP1 (1497 bp) was identified by restriction mapping.

1.2 Construction of the Base Vector OripBR-URA3

The plasmid OripBR-URA3 was composed of two PCR fragments like the plasmid OripBR-TRP1. However, the URA3 yeast gene was used instead of the TRP1 selection marker gene. First PCR reaction: see example 1.1.

The URA3 yeast gene (5' flanking region and the URA3 structural gene) from bp position 75–1030 according to the publication of Rose, M., 1984 was amplified in a second PCR reaction using the primers N5 (SEQ ID NO:5) and N6 (SEQ ID NO.6)

SfiI NotI
        N5: 5'-AAAAAAGGCCATAT GCGGCCGCCGGTAATCTCCGAACAGAAGGA-AGAAC-3'
    XhoI BamHl fd-terminator
        N6: 5'-AAAAAACTCGAGACGAGGATCC ATAAACCGATACAATTAAAGGCTCCTTTTGG-AGCCTTTTTTTTTGGAGAACT TTAGTTTTGCTGGCCGCATCTTCTCAAA-3'
    EndEnd and YEp24 (Botstein, D. et al., 1979) as the template DNA. A singular SfiI cleavage site and NotI cleavage site were introduced by means of the 5' overhanging end of the PCR primer N5 and a second translation stop codon, the fd transcription terminator of the bacteriophage fd (anti-native orientation) from position 1522–1570 (Beck, E. and Zink, B., 1981) and two singular restriction endonuclease cleavage sites (BamHI and XhoI) were introduced at the 3' end of the coding region of the TRP1 structural gene by means of the 5' overhanging end of the PCR primer N6.

The two PCR fragments digested with SfiI and XhoI were ligated after purification by agarose gel electrophoresis. Afterwards the *E. coli* K12 strain CSH28 (Δlacpro, supF, trp, pyrF, his, strA, thi) (source: Cold Spring Harbor Laboratory, New York; Miller, J. H., 1972) was transformed by means of calcium chloride according to the method of Hanahan, D., 1983 or by electroporation according the protocol of Fiedler, S. and Wirth, R., 1988. The transformants were selected on agar plates in M9 minimal medium (preparation: see Sambrook, J. et al., 1989) containing 0.5% (w/v) casamino acids from the Difco Company and 5 mg/ml tryptophan and subsequently grown in liquid culture. The desired plasmid OripBR-URA3 (1697 bp) was identified by restriction mapping.

1.3 Construction of the Antibiotic-resistance-containing Reference Vector OripBR-TET The plasmid OripBR-TET was composed of two PCR fragments like the plasmids OripBR-TRP1 and OripBR-URA3. However, the tetracycline resistance gene (TET) from the plasmid $pBR_{322}$ was used instead of the TRP1 or URA3 selection marker gene. First PCR reaction: see example 1.1.

The TET resistance gene (promoter and the TET structural gene) from bp position 3–1275 according to the publication of Sutcliffe J. G., 1979 was amplified in a second PCR reaction using the primers N7 (SEQ ID NO:7) and N8 (SEQ ID NO:8)

SfiI NotI
        N7: 5'-AAAAAAGGCCATATAGGCCATAT GCGGCCGCCTCATGTTTGACAGCTTATCATC-GATAAG-3'
    XhoI XbaI fd terminator
        N8: 5'-AAAAAACTCGAGATATTCTAGA ATAAACCGATACAATTAAAGGCTCCTTTTGG-AGCCTTTTTTTTTGGAGATCAGGTCGAGGTG-GCCCGGCTCC-3' and $pBR_{322}$ (Sutcliffe, J. G., 1979) as the template DNA. A singular SfiI cleavage site and NotI cleavage site were introduced by means of the 5' overhanging end of the PCR primer N7 and the fd transcription terminator of the bacteriophage fd (anti-native orientation) from position 1522–1570 (Beck, E. and Zink, B., 1981) and two singular restriction endonuclease cleavage sites (XhoI and XbaI) were introduced at the 3' end of the coding region of the TET structural gene by means of the 5' overhanging end of the PCR primer N8.

The two PCR fragments digested with SfiI and XhoI were ligated after purification by agarose gel electrophoresis. Afterwards the *E. coli* K12 strain JA300 (thr, leuB6, thi, thyA, trpC1117, hsrK, HsmK, strR; DSMZ 4776) (source: "Deutsche Sammlung für Mikroorganismen und Zellkulturen GmbH) was transformed by means of calcium chloride according to the method of Hanahan, D., 1983 or by electroporation according the protocol of Fiedler, S. and Wirth, R., 1988. The transformants were selected (agar plates) in LB complete medium (preparation: see Sambrook, J. et al., 1989) containing 12.5 μg/ml tetracycline and subsequently grown in liquid culture. The desired plasmid OripBR-TET (2012 bp) was identified by restriction mapping.

1.4 Removal of an NdeI Cleavage Site in the Plasmids OripBR-TRP1, OripBR-URA3 and OripBR-TET An undesired NdeI cleavage site which was formed from the 2 PCR fragments between the cleavage sites NotI and SfiI during ligation of the base vectors OripBR-TRP1, OripBR-URA3 and OripBR-TET, was subsequently removed by means of an NotI/SfiI nucleotide adapter.

For this the plasmids OripBR-TRP1, OripBR-URA3 and Orip-BR-TET were digested with NotI and SfiI, the vector fragments were purified by agarose gel electrophoresis and ligated with an NotI/SfiI nucleotide adapter. The desired plasmids were identified by restriction mapping (missing NdeI cleavage site).

The NotI/SfiI adapter was prepared by hybridization from the mutually complementary oligonucleotides N9 (SEQ ID NO:9) and N10 (SEQ ID NO:10). For this 10 nmol of each of the oligonucleotides N9 and N10 were mixed in 100 μl 12.5 mmol/l Tris-HCl, pH 7.0 and 12.5 mmol/l MgCl$_2$, the mixture was heated for 5 min to 95° C. and subsequently slowly cooled to room temperature.

N9: 5'-AGGCCGGGGGGGGGC-3'

N10. 5'-GGCCGCCCCCCCCCGGCCTATA-3'

NotI/SfiI adapter

N9 5'-AGGCCGGGGGGGGGC-3'
3-ATATCCGGCCCCCCCCCGCCGG-5'N10
SfiI NotI

EXAMPLE 2

Construction of the Prokaryotic Expression Cassette

The expression cassette that was used (heterologous transcription unit) was composed of the following elements:

i) the regulated T5-P$_{N25/03/04}$ hybrid promoter (Bujard, H. et al, 1987; Stüber, D. et al, 1990), ii) a synthetic ribosomal binding site RBSII (Stüber, D. et al., 1990), iii) a multiple cloning cleavage site with the singular cleavage sites NdeI, SalI, XmaI, EcoRV and CelII and iv) the λ-T0 bacteriophage transcription terminator (Schwarz, E. et al., 1978).

Figure 3:
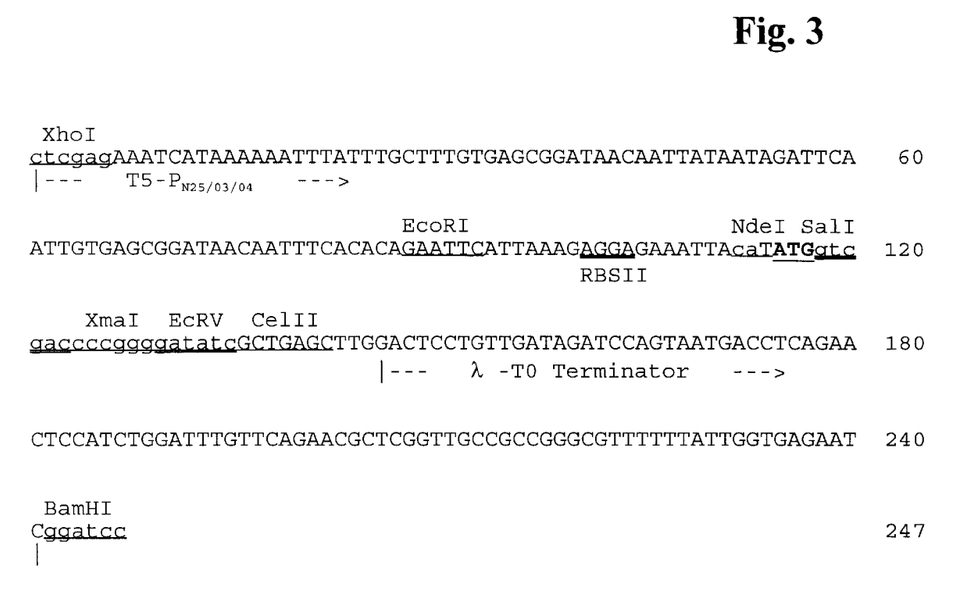
FIG. 3: Nucleotide sequence [SEQ ID NO:24] of the expression cassette composed of the T5-$P_{N25/03/04}$ hybrid promoter, the ribosomal binding site RBSII, a multiple cloning cleavage site (NdeI/SalI/XmaI/EcoRV/CellII) and the λ-T0 terminator.

The T5-P$_{N25/03/04}$ hybrid promoter (FIG. 3: bp position: 1–87) was linked to the λ-T0 terminator (FIG. 3: bp position: 146–241) by means of an EcoRI-RBSII-NdeI/SalV/XmaI/EcoRV/CelII linker.

The expression cassette was obtained by reconstruction of a pDS56/RBSII plasmid (Stüber, D. et al., 1990). For this a derivative of the pDS56/RBSII plasmid was digested with EcoRI and CelII and the EcoRI/CelII-pDS56 vector fragment purified by agarose gel electrophoresis was ligated with an EcoRI-RBSII-NdeI/SalI/XmaI/EcoRV/CelII linker.

The EcoRI-RBSII-NdeI/SalI/XmaI/EcoRV/CelII linker was prepared by hybridization from the mutually complementary oligonucleotides N11 (SEQ ID NO:11) and N12 (SEQ ID NO:12). 10 nmol of each of the oligonucleotides N11 and N12 were mixed in 100 μl 12.5 mmol/l Tris-HCl, pH 7.0 and 12.5 mmol/l MgCl$_2$, the mixture was heated for 5 min to 95° C. and then slowly cooled to room temperature.
N11:
5'-CATTAAAGAGGAGAAATTAACTATGGTATGGTCG-ACCCCGGGGATATCGC-3'

N12:
5'-TCAGCGATATCCCCGGGGTCGACCATACCAT-AGTTAATTTCTCCTCTTTAATGAATT-3'
EcoRI-RBSII-NdeI/SalI/XmaI/EcoRV/CelII linker
NdeI SalI XmaI EcoRV
N11 5'-CATTAAAGAGGAGAAATTAACTATGGTATG
GTCGACCCCGGGGATATCGC-3'

3'-TTAAGTAATTTCTCCTCTTTAATTGATACCATAC-CAGCTGGGGCCCCTATAGCGACT-5'N12
EcoRI CelII

The desired plasmid p16074a was identified by restriction mapping and the expression cassette was checked by DNA sequencing.

EXAMPLE 3

Construction of the Expression Plasmids OripBR-TRP1-EK, OripBR-URA3-EK and OripBR-TET-EK The expression cassette (FIG. 3) of the plasmid p16074a composed of the regulated T5-P$_{N}$25/03/04 hybrid promoter, the synthetic ribosomal binding site RBSII, a multiple cloning cleavage site with the singular cleavage sites NdeI, SalI, XmaI, EcoRV and CelII and the λ-T0 terminator was amplified by PCR and inserted into the plasmids OripBR-TRP1, OripBR-URA3 and OripBR-TET.

3.1 Construction of the Expression Plasmid OripBR-TRP1-EK

The expression cassette (FIG. 3) was amplified by means of PCR using the primers N13 (SEQ ID NO:13) and N14 (SEQ ID NO:14)

N13: 5'-AAAAAAGTAAAGGGGCTTTTCACGG-3'

N14:
5'-AAAAAAGGATCCGATTCTCACCAATAAAAA-ACGCCCG-3'
BamHI and the plasmid p16074a as template DNA. A singular BainHI cleavage site was introduced at the 3' end of the expression cassette (λ-T0 terminator) by means of the PCR primer N14. The PCR product was digested with the restriction endonucleases XhoI and BamHI and the ca. 255 bp long XhoI/BamHI fragment was ligated after purification by agarose gel electrophoresis into the ca. 1490 bp long XhoI/BamHI-OripBR-TRP1 vector fragment (example 2). The desired plasmid OripBR-TRP1-EK (1728 bp) was identified by restriction mapping and the sequence of the expression cassette amplified by PCR was verified by DNA sequencing.

3.2 Construction of the Expression Plasmid OripBR-URA3-EK

The expression plasmid OripBR-URA3-EK (1928 bp) was prepared analogously to the plasmid OripBR-TRP1-EK. However, the base vector OripBR-URA3 was used instead of the base vector OripBR-TRP 1.

3.3 Construction of the Reference Plasmid OripBR-TET-EK

The expression cassette (FIG. 3) was amplified by means of PCR using the primers N13 (SEQ ID NO:13) and N14 (SEQ ID NO:15)

N15: 5'-AAAAAA TCTAGAGATTCTCACCAATAAAAAACGCCCG-3'
XbaI and the plasmid p16074a as template DNA. A singular XbaI cleavage site was introduced at the 3' end of the expression cassette (λ-T0 terminator) by means of the PCR primer N15. The PCR product was digested with the restriction endonucleases XhoI and XbaI and the ca. 255 bp long XhoI/XbaI fragment was ligated after purification by agarose gel electrophoresis into the ca. 2000 bp long XhoI/XbaI-OripBR-TET vector fragment (example 2). The desired plasmid OripBR-TET-EK (2243 bp) was identified by restriction mapping and the sequence of the expression cassette amplified by PCR was verified by DNA sequencing.

EXAMPLE 4

Construction of the Expression Plasmids OripUC-TRP1-EK, OripUC-URA3-EK and OripUC-TET-EK The medium copy number origin of replication of the plasmid pBR322 was substituted by the high copy number origin of replication of a pUC plasmid in the plasmids OripUC-TRP1-EK, OripUC-URA3-EK and OripUC-TET-EK.

For this the pUC origin of replication was amplified by means of a PCR using the primers N1 (SEQ ID NO:1) and N2 (SEQ ID NO:2) (example 1) and the plasmid pUC20 as template DNA.

The ca. 650 bp long SfiI/NotI-pUC origin of replication fragment digested with SfiI and NotI was ligated after purification by agarose gel electrophoresis into the corresponding vector fragments SfiI/NotI-OripBR-TRP1-EK, SfiI/NotI-OripBR-URA3-EK and SfiI/NotI-OripBR-TET-EK. The desired plasmids OripUC-TRP1-EK, OripUC-URA3-EK and OripUC-TET-EK were identified on the basis of their increased plasmid copy number (3–5-fold increase in plasmid yield after standard preparation).

EXAMPLE 5

Construction of IFN-α2b Expression Plasmids 5.1 Synthesis of the Interferon-α2b Model Gene The expression vectors were tested with regard to plasmid stability and IFN-α2b synthesis using an interferon-α2b gene (Met-IFN-α2b structural gene without a signal sequence) as a model gene that has to be expressed heterologously.

The chemically prepared Met-IFN-α2b structural gene is based on the amino acid sequence stated in the Index Nominum (International Drug Directory 1992/1993) for mature IFN-α2b. The Met-IFN-α2b structural gene additionally contains an ATG start codon. The synthetic ribosomal RBSII binding site and a singular EcoRI cleavage site are located upstream at the 5' end of the Met-IFN-α2b structural gene (Stüber D. et al., 1990). The codons that are preferably used in E. coli (E. coli codon usage) were taken into consideration in the gene design of the Met-IFN-α2b gene. In addition suitable singular restriction endonuclease cleavage sites were introduced within the coding region and at the ends of the Met-IFN-α2b structural gene (EcoRI and HindIII) with regard to the construction of variant genes and recloning the Met-IFN-α2b DNA segment.

The IFN-α2b gene (RBSII-Met-IFN-α2b gene) was prepared by the Genosys Company (Genosys Biotechnologies Inc. Cambridge, England) from oligonucleotides made by chemical synthesis. The double-stranded RBSII-Met-IFN-α2b gene was assembled by annealing and ligation of the oligonucleotides and subsequently cloned into the EcoRI and HindIII cleavage site of the E. coli standard vector pBluescriptSK(+) from the Stratagene Company (Stratagene GmbH, Heidelberg, Germany). The predetermined DNA sequence of the cloned RBSII-Met-IFN-α2b structural gene was confirmed by DNA sequencing. Subsequently the ca. 535 bp long EcoRI/HindIII-RBSII-Met-IFN-α2b segment was recloned into a pDS56/RBSII plasmid digested with EcoRI and HindIII (pDS-IFN). This enables the transfer of the RBSII-Met-IFN-α2b gene in the form of a ca. 540 bp long EcoRI/CelII-RBSII-Met-IFN-α2b fragment.

5.2 Construction of the IFN-α2b Expression Plasmids

The RBSII-Met-IFN-α2b gene was isolated from the plasmid pDS-IFN in the form of a ca. 540 bp long EcoRI/CelII-RBSII-Met-IFN-α2b fragment and subsequently ligated into each of the plasmids OripBR-TRP1-EK, OripBR-URA3-EK, OripBR-TET-EK, OripUC-TRP1-EK, OripUC-URA3-EK and OripUC-TET-EK that were digested with EcoRI and CelII. The desired plasmids OripBR-TRP1-EK-IFN, OripBR-URA3-EK-IFN, OripBR-TET-EK-IFN, OripUC-TRP1-EK-IFN, OripUC-URA3-EK-IFN and OripUC-TET-EK-IFN were identified by restriction mapping.

EXAMPLE 6

Construction of Non-revertible trpC and pyrF E. coli Host Strains

The desired auxotrophy markers trpC and pyrF were introduced into already available laboratory strains by directed deletion of the complete gene or of a larger gene fragment by means of homologous recombination according to the method of Hamilton C. M. et al. 1989.

6.1 Construction of the Deletion Plasmids 6.1.1. Construction of the deletion plasmid pMAK705-trpD/B In order to delete the complete chromosomal trpC gene (1355 bp), 700–800 bp of the 5' flanking region (trpD) and of the 3' flanking region (trpB) were each cloned by means of PCR and these were ligated into the vector pMAK705 (Hamilton C. M. et al., 1989) in direct fusion (trpD/B) by means of a common cleavage site (NotI) introduced by the PCR primers. The DNA sequence of the tryptophan operon of E. coli is given by Yanofsky, C. et al., 1981.

The 5' flanking region of the trpC gene (trpD) was amplified using the primers N16 (SEQ ID NO:16) and N17 (SEQ ID NO:17)

N16: 5'-AAAAAA GGATCCGGGCTGAAAGTGGCGAAACACGGC-3'
BamHI

N17: 5'-AAAAAA GCGGCCGCTTACCCTCGTGCCGCCAGTGCG-3'
NotI and chromosomal E. coli DNA as a template. A singular BamHI cleavage site was introduced at the 5' end by means of the primer N16 and a singular NotI cleavage site was introduced at the 3' end of the amplified trpD fragment by means of the primer N17.

The 3' flanking region of the trpC gene (trpB) was amplified using the primers N18 (SEQ ID NO:18) and N19 (SEQ ID NO:19)

N18: 5'-AAAAAA GCGGCCGCGGAAAGGAACAATGACAACATTAC TTAAC-3'
NotI

N19: 5'-AAAAAA GCATGCCGGTGCGCCGTGCTCGCCAGTTTCG-3'
SpHI and chromosomal E. coli DNA as a template. A singular NotI cleavage site was introduced at the 5' end by means of the primer N18 and a singular SpHI cleavage site was introduced at the 3' end of the amplified trpB fragment by means of the primer N19.

The trpD PCR fragment was digested with BamHI and NotI (ca. 710 bp) and the trpB PCR fragment was digested with NotI and SpHI (ca. 820 bp). After purification by agarose gel electrophoresis, the DNA fragment was ligated into the ca. 5650 bp long BamHI/SpHI-pMAK705 vector fragment by means of a three fragment ligation in a direct fusion via the common NotI cleavage site. The desired plasmid pMAK705-trpD/B (7104 bp) was identified by restriction mapping and the trpD/B sequence amplified by PCR was verified by DNA sequencing.

6.1.2 Construction of the deletion plasmid pMAK705-ΔpyrF

In order to delete ca. 260 bp from the coding region of the chromosomal pyrF gene, 700–800 bp of the flanking pyrF region was cloned in each case by means of PCR and ligated in a direct fusion (ΔpyrF) into the vector pMAK705 by means of a common cleavage site (XbaI) introduced by the PCR primers. The DNA sequence of the pyrF operon of *E. coli* was published by Turnbough, C. L. Jr. et al., 1987. The 5' flanking region of the ΔpyrF gene was amplified using the primers N20 (SEQ ID NO:20) and N21 (SEQ ID NO:21)

N20: 5' AAAAA GGATCCGTACGTAGTAAGCCTCGTTATCGTTG-3'
BamHII

N21: 5'-AAAAAA TCTAGACACACGCCTAAGTCAGCTGCAGC-3'
XbaI and chromosomal *E. coli* DNA as a template. A singular BamHI cleavage site was introduced at the 5' end by means of the primer N20 and a singular XbaI cleavage site was introduced at the 3' end of the amplified DNA fragment by means of the primer N21.

The 3' flanking region of the ΔpyrF gene was amplified using the primers N22 (SEQ ID NO:22) and N23 (SEQ ID NO:23)

N22: 5'-AAAAAA TCTAGAGGTCAGGAGTTCAAACTGGTTACG-3'
XbaI

N23: 5'-AAAAAA GCATGCCAGCTGTCGGAGGTGTTATTGGTC-3'
SpHI and chromosomal *E. coli* DNA as a template. A singular XbaI cleavage site was introduced at the 5' end by means of the primer N22 and a singular SpHI cleavage site was introduced at the 3' end of the amplified DNA fragment by means of the primer N23.

The 5' flanking ΔpyrF fragment was digested with BamHI and XbaI (ca. 600 bp) and the 3' flanking ΔpyrF fragment was digested with XbaI and SpHI (ca. 690 bp). After purification by agarose gel electrophoresis, the DNA fragments were ligated in a direct fusion into the ca. 5650 bp long BamHI/SpHI-pMAK705 vector fragment by means of a three fragment ligation via the common XbaI cleavage site. The desired plasmid pMAK705-ΔpyrF (6788 bp) was identified by restriction mapping and the pyrF sequence amplified by PCR was verified by DNA sequencing.

6.2 Isolation of *E. coli* Deletion Mutants

The vector pMAK705 is characterized by a temperature-sensitive origin of replication (origin of replication from pSC101) which is inactive at 44° C. and by a chloramphenicol resistance gene. In order to delete a chromosomal gene the appropriate pMAK705 plasmid derivative is transformed in the desired *E. coli* strain. A prerequisite for a homologous recombination between the plasmid and *E. coli* chromosome is a recombination-competent *E. coli* strain (recA$^+$ genotype). Strains whose genotype is recA$^-$ cannot carry out a homologous recombination and are therefore unsuitable.

The *E. coli* K12 strain UT5600 (ara, proC-14, leuB6, azi-6, lacY1, tsx-67, entA403, trpE38$^+$, rpsL109, xyl-5, mtl-1, thi-1, ΔompT) (Grodberg, J. and Dunn, J. J., 1988) was transformed with the plasmid pMAK705-trpD/B and with the plasmid pMAK705-ΔpyrF. After addition of the plasmid DNA, the transformation preparation was incubated for 30 minutes on ice, for 5 minutes at 37° C. (heat shock) and for 30 minutes at 30° C. The transformation preparation was transferred to 3 ml LB medium containing 20 μg/ml chloramphenicol and the cells were cultured overnight.

In order to select for plasmid cointegrates, i.e. for cells which have integrated the plasmid into the chromosome by means of homologous recombination, 300 μl of a 10$^{-5}$ dilution of the overnight culture was plated out on LB agar plates containing 20 μg/ml chloroamphenicol. The agar plates were preheated to 50–60° C. in an incubator and, after plating out the cells, were immediately incubated at exactly 44° C. Since the pMAK705 plasmid does not replicate at this temperature, only those cells grow into colonies which have chromosomally integrated the plasmid. The cointegrate candidates were subsequently passaged 2 to 3 times on LB agar plates containing 20 μg/ml chloramphenicol at 44° C. for purification (dilution smear).

In order to break up the cointegrates and to cure the plasmid that disintegrated from the chromosome, a purified cointegrate clone was cultured for several passages (2 to 6) in LB medium at 30° C. in the absence of chloramphenicol. Afterwards the cells were separated by dilution on LB medium and tested for the desired genotype.

6.2.1. Characterization of the deletion mutant UT5600 (ΔtrpC)

The cells/clones separated by dilution on LB medium were analysed with regard to the desired trp auxotrophy by plating out on medium (M9 minimal medium containing 0.5% casamino acids) with tryptophan (50 mg/ml) and without tryptophan (replica plating). In addition the chloramphenicol sensitivity of the clones was checked by plating out on LB medium with chloramphenicol (20 μg/ml) and without cloramphenicol. In addition the chromosomal trpC deletion was confirmed by comparative PCR analysis between the initial strain and deletion mutant using the PCR primers N1 and N4 and the corresponding chromosomal DNA as template DNA. The PCR product of the initial strain was ca. 2900 bp long as calculated theoretically and that of the trpC deletion mutant was ca. 1430 bp long.

6.2.2. Characterization of the deletion mutant UT5600 (ΔpyrF)

The cells/clones separated by dilution on LB medium were analysed with regard to the desired pyrF auxotrophy by plating out on medium (M9 minimal medium containing 0.5% casarnino acids) with uracil (20 mg/ml) and without uracil. In addition the chloramphenicol sensitivity of the clones was checked by plating out on LB medium with chloramphenicol (20 μg/ml) and without cloramphenicol. In addition the chromosomal pyrF deletion was confirmed by comparative PCR analysis between the initial strain and deletion mutant using the PCR primers N5 and N8 and the corresponding chromosomal DNA as template DNA. The PCR product of the initial strain was ca. 1550 bp long as calculated theoretically and that of the pyrF deletion mutant was ca. 1290 bp long.

EXAMPLE 7

Expression of a Heterologous Model Gene (IFN-α2b)

The new host/vector system based on antibiotic-free selection by complementation of an auxotrophy was evaluated with regard to its function and performance using interferon-α2b as a model gene that has to be expressed heterologously.

7.1 Selection by Complementation of the trpC Auxotrophy

In order to express the IFN-α2b gene, the *E. coli* K12 strain UT5600 (ΔtrpC) (example 6) was transformed in each case with one of the expression plasmids OripBR-TRP1-EK-IFN, OripUC-TRP1-EK-IFN, OripBR-TET-EK-IFN and OripUC-TET-EK-IFN described in example 5. The transformed UT5600(ΔtrpC)/OripBR-TRP1-EK-IFN and UT5600 (ΔtrpC)/OripUC-TRP1-EK-IFN cells were grown at 37° C. in a shaking culture in M9 minimal medium containing 0.5% casamino acids (Difco) and the reference cells UT5600 (ΔtrpC)/OripBR-TET-EK-IFN and OripUC-TET-EK-IFN were grown in M9 minimal medium containing 0.5% casamino acids (Difco) and 50 mg/ml tryptophan and 12.5 μg/ml tetracycline at 37° C. up to an optical density at 550 nm ($OD_{550}$) of 0.6–0.9 and subsequently induced with IPTG (1–5 mmol/l final concentration). After an induction phase of 4–8 hours (h) at 37° C., the cells were harvested by centrifugation (Sorvall RC-5B centrifuge, GS3 rotor, 6000 rpm, 15 min), washed with 50 mmol/l Tris-HCl buffer, pH 7.2 and stored at −20° C. until further processing.

7.2 Selection by Complementation of the pyrF Auxotrophy

In order to express the IFN-α2b gene, the *E. coli* K12 strain UT5600 (ΔpyrF) (example 6) was transformed in each case with one of the expression plasmids OripBR-URA3-EK-IFN, OripUC-URA3-EK-IFN, OripBR-TET-EK-IFN and OripUC-TET-EK-IFN described in example 5. The transformed UT5600(ΔtrpC)/OripBR-URA3-EK-IFN and UT5600 (ΔtrpC)/OripUC-URA3-EK-IFN cells were grown at 37° C. in a shaking culture in M9 minimal medium containing 0.5% casamino acids (Difco) and the reference cells UT5600 (ΔtrpC)/OripBR-TET-EK-IFN and OripUC-TET-EK-IFN were grown in M9 minimal medium containing 0.5% casamino acids (Difco) and 20 mg/ml uracil and 12.5 μg/ml tetracycline at 37° C. up to an optical density at 550 nm ($OD_{550}$) of 0.6–0.9 and subsequently induced with IPTG (1–5 mmol/l final concentration). After an induction phase of 4–8 hours (h) at 37° C., the cells were harvested by centrifugation (Sorvall RC-5B centrifuge, GS3 rotor, 6000 rpm, 15 min), washed with 50 mmol/l Tris-HCl buffer, pH 7.2 and stored at −20° C. until further processing.

7.3 Expression Analysis in the Standard System

The synthesis of IFN-α2b was analysed in the UT5600 (ΔtrpC) or UT5600 (ΔpyrF) cells transformed with the expression plasmids OripBR-TRP1-EK-IFN, OripUC-TRP1-EK-IFN, OripBR-URA3-EK-IFN, OripUC-URA3-EK-IFN, OripBR-TET-EK-IFN and OripUC-TET-EK-IFN. For this cell pellets from 3 $OD_{550}$ units (1 $OD_{550}$=1 ml cell suspension with an $OD_{550}$ of 1) of centrifuged culture medium was resuspended in 0.25 ml 10 mmol/l Tris-HCl, pH 7.2 and the cells were lysed by ultrasonic treatment (2 pulses of 30 s at 50% intensity) with a Sonifier® Cell Disruptor B15 from the Branson Company (Heusenstamm, Germany). The insoluble cell components were sedimented (Eppendorf 5415 centrifuge, 14000 rpm, 5 min) and the supernatant was admixed with ⅕ volumes (vol) 5×SDS sample buffer (1×SDS sample buffer: 50 mmol/l Tris-HCl, pH 6.8, 1% SDS, 1% mercaptoethanol, 10% glycerol, 0.001% bromophenol blue). The insoluble cell debris fraction (pellet) was resuspended in 0.3 ml 1×SDS sample buffer containing 6–8 M urea, the samples were incubated for 5 min at 95° C. and again centrifuged. Subsequently the proteins were separated by SDS polyacrylamide gel electrophoresis (PAGE) (Laemmli, U. K., 1970) and stained with Coomassie Brilliant Blue R dye.

The synthesized IFN-α2b protein was homogeneous and was found exclusively in the insoluble cell debris fraction in the form of insoluble protein aggregates, the so-called inclusion bodies (IBs). The expression yield was comparable within the scope of the measurement accuracy in all clones/cells and was between 30–50% relative to the total *E. coli* protein.

EXAMPLE 8

Examination of the Plasmid Stability

A sample was taken before induction of the cells (example 7) and a plasmid stability test was carried out. For this the samples were diluted directly with M9 minimal medium containing 0.5% casamino acids and 300 μl of each dilution step was plated out on a non-selective agar plate (M9 minimal medium supplemented with 0.5% casamino acids, 50 mg/ml tryptophan and 20 mg/l uracil). Subsequently 400 individual colonies from each clone were firstly smeared with a toothpick on an appropriate selective agar plate (M9 minimal medium containing 0.5% casamino acids or M9 minimal medium supplemented with 0.5% casamino acids, 50 mg/l tryptophan, 20 mg/ml uracil and 12.5 μg/ml tetracycline) and then on a non-selective agar plate (M9 minimal medium supplemented with 0.5% casamino acids, 50 mg/l tryptophan and 20 mg/l uracil).

The number of plasmid-containing cells was determined from the number of cells which formed a colony on both agar plates. Cells which do not grow on the selective agar plate have lost the plasmid for complementing the auxotrophy or forming the antibiotic-resistance (TET reference plasmids). Before induction of the cells the plasmid stability was 100% for all cultures independent of the selection method and independent of the plasmid type.

What is claimed is:

1. A prokaryotic expression vector for use in a host cell which comprises:
   a) a prokaryotic origin of replication;
   b) at least one eukaryotic auxotrophy marker gene which encodes an enzyme required for the sythesis of a product necessary for the survival of an auxotrophic prokaryote under the control of a eukaryotic promoter;
   c) a foreign gene under the direct control of a prokaryotic promoter, such that the mRNA of the foreign gene is formed; and
   d) one or more transcription terminators;
which prokaryotic expression vector contains no more than fifty consecutive base pairs of a host cell sequence.

2. The prokaryotic expression vector of claim 1, which vector further comprises a ribosomal binding site and a multiple cloning site.

3. The prokaryotic expression vector of claim 1 wherein the auxotrophy marker gene and the foreign gene are oriented in opposite directions with the transcription terminator located between the auxotrophy marker gene and the foreign gene so positioned as to terminate transcription of both genes.

4. The prokaryotic expression vector of claim 1 wherein the auxotrophy marker gene is a yeast gene.

5. The prokaryotic expression vector of claim 3 wherein the auxotrophy marker gene is a yeast gene.

6. The prokaryotic expression vector of claim 5 wherein the auxotrophy marker gene is URA3 or TRP 1.

7. The prokaryotic expression vector of claim 6 wherein the auxotrophic marker gene is expressed from the 5' flanking region of the URA3 or TRP1 gene.

8. The prokaryotic expression vector of claim 7 wherein the prokaryotic promoter is T5-P N25/03/04.

9. The prokaryotic expression vector of claim 8 wherein the transcription terminator is derived from bacteriophage fd or λ-T0.

10. The prokaryotic expression vector of claim 9 wherein the origin of replication is derived from pBR or pUC plasmids.

11. A prokaryotic auxotrophic host cell comprising the prokaryotic expression vector of claim 1, which host cell has at least one mutation such that it is unable to express the product expressed by the auxotrophic marker gene.

12. The prokaryotic host cell of claim 11 which is an *E. coli* cell.

13. The prokaryotic host cell of claim 12 which is unable to produce the product of one of the trpC gene or the pyrF gene.

14. The prokaryotic host cell of claim 13 which comprises the prokaryotic expression vector of claim 1 wherein the auxotrophy marker gene is URA3 or TRP1, and wherein the auxotrophy marker gene and the foreign gene are oriented in opposite directions, with the transcription terminator located between the auxotrophy marker gene and the foreign gene, so positioned as to terminate transcription of both genes.

15. The prokaryotic host cell of claim 14 which produces sufficient amounts of the product of the genes URA3 or TRP1 to survive on minimal medium but does not produce an amount of such gene product which constitutes more than 1.0% of the total amount of protein produced by the cell.

16. A method for producing a recombinant protein which comprises expressing a gene encoding said recombinant protein under the direct control of a prokaryotic promoter in a prokaryotic expression vector, which prokaryotic expression vector contains no more than fifty consecutive base pairs of a host cell sequence, wherein said prokaryotic expression vector additionally comprises a prokaryotic origin of replication; at least one eukaryotic auxotrophy marker gene which encodes an enzyme required for the synthesis of a product necessary for the survival of an auxotrophic prokaryote under the control of a eukaryotic promoter; and one or more transcription terminators.

* * * * *

SEQUENCE LISTING

<160> NUMBER OF SEQ ID NOS: 24

<210> SEQ ID NO 1
<211> LENGTH: 41
<212> TYPE: DNA
<213> ORGANISM: Artificial Sequence
<220> FEATURE:
<223> OTHER INFORMATION: Description of Artificial Sequence:primer

<400> SEQUENCE: 1

```
aaaaaaggcc atataggccg gccgcgttgc tggcgttttt c                41
```

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence:primer

<400> SEQUENCE: 2

```
aaaaaactcg aggagcgtca gaccccgtag aaaag                       35
```

<210> SEQ ID NO 3
<211> LENGTH: 53
<212> TYPE: DNA
<213> ORGANISM: Artificial Sequence
<220> FEATURE:
<223> OTHER INFORMATION: Description of Artificial Sequence:primer

<400> SEQUENCE: 3

```
aaaaaaggcc atataggcca tatgcggccg cggagagggc aagagggag ggc    53
```

<210> SEQ ID NO 4
<211> LENGTH: 104
<212> TYPE: DNA
<213> ORGANISM: Artificial Sequence
<220> FEATURE:
<223> OTHER INFORMATION: Description of Artificial Sequence:primer

<400> SEQUENCE: 4

```
aaaaaactcg agatatggat cctctccaaa aaaaaggct ccaaaaggag cctttaattg    60
tatcggttta tttactattt cttagcattt ttgacgaaat ttgc                   104
```

<210> SEQ ID NO 5
<211> LENGTH: 58
<212> TYPE: DNA
<213> ORGANISM: Artificial Sequence
<220> FEATURE:
<223> OTHER INFORMATION: Description of Artificial Sequence:primer

<400> SEQUENCE: 5

```
aaaaaaggcc atataggcca tatgcggccg ccggtaatct ccgaacagaa ggaagaac    58
```

<210> SEQ ID NO 6
<211> LENGTH: 102
<212> TYPE: DNA
<213> ORGANISM: Artificial Sequence
<220> FEATURE:
<223> OTHER INFORMATION: Description of Artificial Sequence:primer

<400> SEQUENCE: 6

```
aaaaaactcg agacgaggat ccataaaccg atacaattaa aggctccttt tggagccttt    60
ttttttggag aactttagtt ttgctggccg catcttctca aa                     102
```

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence:primer

<400> SEQUENCE: 7

```
aaaaaaggcc atataggcca tatgcggccg cctcatgttt gacagcttat catcgataag    60
```

```
<210> SEQ ID NO 8
<211> LENGTH: 94
<212> TYPE: DNA
<213> ORGANISM: Artificial Sequence
<220> FEATURE:
<223> OTHER INFORMATION: Description of Artificial Sequence:primer

<400> SEQUENCE: 8
aaaaaactcg agatattcta gaataaaccg atacaattaa aggctccttt tggagccttt      60 tttttggag atcaggtcga ggtggcccgg ctcc                                  94

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence:primer

<400> SEQUENCE: 9
aggccggggg ggggc                                                      15

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 10
ggccgccccc ccccggccta ta                                              22

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence:primer

<400> SEQUENCE: 11
cattaaagag gagaaattaa ctatggtatg gtcgaccccg gggatatcgc                50

<210> SEQ ID NO 12
<211> LENGTH: 57
<212> TYPE: DNA
<213> ORGANISM: Artificial Sequence
<220> FEATURE:
<223> OTHER INFORMATION: Description of Artificial Sequence:primer

<400> SEQUENCE: 12
tcagcgatat ccccggggtc gaccatacca tagttaattt ctcctcttta atgaatt        57

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 13
aaaaaagtaa agggctttt cacgg                                            25

<210> SEQ ID NO 14
<211> LENGTH: 37
<212> TYPE: DNA
<213> ORGANISM: Artificial Sequence
<220> FEATURE:
```

```
<223> OTHER INFORMATION: Description of Artificial Sequence:primer

<400> SEQUENCE: 14
aaaaaaggat ccgattctca ccaataaaaa acgcccg                              37

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence:primer

<400> SEQUENCE: 15
aaaaaatcta gagattctca ccaataaaaa acgcccg                              37

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence:primer

<400> SEQUENCE: 16
aaaaaaggat ccgggctgaa agtggcgaaa cacggc                               36

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence:primer

<400> SEQUENCE: 17
aaaaaagcgg ccgcttaccc tcgtgccgcc agtgcg                               36

<210> SEQ ID NO 18
<211> LENGTH: 43
<212> TYPE: DNA
<213> ORGANISM: Artificial Sequence
<220> FEATURE:
<223> OTHER INFORMATION: Description of Artificial Sequence:primer

<400> SEQUENCE: 18
aaaaaagcgg ccgcggaaag gaacaatgac aacattactt aac                       43

<210> SEQ ID NO 19
<211> LENGTH: 37
<212> TYPE: DNA
<213> ORGANISM: Artificial Sequence
<220> FEATURE:
<223> OTHER INFORMATION: Description of Artificial Sequence:primer

<400> SEQUENCE: 19
aaaaaagcat gccggtgcgc cgtgctcgcc agtttcg                              37

<210> SEQ ID NO 20
<211> LENGTH: 38
<212> TYPE: DNA
<213> ORGANISM: Artificial Sequence
<220> FEATURE:
<223> OTHER INFORMATION: Description of Artificial Sequence:primer

<400> SEQUENCE: 20
aaaaaaggat ccgtacgtag taagcctcgt tatcgttg                             38
```

```
<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence:primer

<400> SEQUENCE: 21
aaaaaatcta gacacacgcc taagtcagct gcagc                                  35

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence:primer

<400> SEQUENCE: 22
aaaaaatcta gaggtcagga gttcaaactg gttacg                                 36

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence:primer

<400> SEQUENCE: 23
aaaaaagcat gccagctgtc ggaggtgtta ttggtc                                 36

<210> SEQ ID NO 24
<211> LENGTH: 247
<212> TYPE: DNA
<213> ORGANISM: Artificial Sequence
<220> FEATURE:
<223> OTHER INFORMATION: Description of Artificial Sequence:expression
      cassette

<400> SEQUENCE: 24
ctcgagaaat cataaaaaat ttatttgctt tgtgagcgga taacaattat aatagattca        60
attgtgagcg gataacaatt tcacacagaa ttcattaaag aggagaaatt acatatggtc       120
gaccccgggg atatcgctga gcttggactc ctgttgatag atccagtaat gacctcagaa       180
ctccatctgg atttgttcag aacgctcggt tgccgccggg cgttttttat tggtgagaat       240
cggatcc                                                                247
```